US006743772B1

(12) United States Patent
Broliden et al.

(10) Patent No.: US 6,743,772 B1
(45) Date of Patent: *Jun. 1, 2004

(54) USE OF PAROVIRUS CAPSID PARTICLES IN THE INHIBITION OF CELL PROLIFERATION AND MIGRATION

(76) Inventors: Kristina Broliden, Skogsviksvägen 51, S-182 39 Danderyd (SE); Magnus Westgren, Skillinggränd 5, S-112 20 Stockholm (SE)

( * ) Notice: Subject to any disclaimer, the term of this patent is extended or adjusted under 35 U.S.C. 154(b) by 18 days.

This patent is subject to a terminal disclaimer.

(21) Appl. No.: 10/200,616

(22) Filed: Jul. 19, 2002

Related U.S. Application Data

(63) Continuation of application No. 09/447,693, filed on Nov. 23, 1999, now abandoned.

(30) Foreign Application Priority Data

Nov. 24, 1998 (SE) ................................................ 9804022

(51) Int. Cl.$^7$ .......................... A61K 38/00; A61K 39/12; C07K 14/015; C12N 7/00

(52) U.S. Cl. ........................ 514/2; 530/350; 424/204.1; 424/233.1; 435/5; 435/235.1; 435/236

(58) Field of Search .............................. 424/93.2, 93.6, 424/184.1, 185.1, 186.1, 199.1, 204.1, 233.1; 435/5, 69.1, 69.3, 440, 456, 235.1, 236, 320.1; 514/2, 44; 530/300, 350; 536/23.7, 23.72

(56) References Cited

U.S. PATENT DOCUMENTS

| | | | |
|---|---|---|---|
| 4,612,337 A | 9/1986 | Fox, Jr. et al. ............. 523/113 |
| 4,818,540 A | 4/1989 | Chien et al. ................. 424/448 |
| 4,908,773 A | 3/1990 | Pantoliano et al. ......... 364/495 |
| 5,288,707 A | 2/1994 | Metternich ................... 514/19 |
| 5,508,186 A | 4/1996 | Takashi et al. ............. 435/235 |
| 5,552,534 A | 9/1996 | Hirschmann et al. ....... 536/17.4 |
| 5,811,515 A | 9/1998 | Grubbs et al. .............. 530/330 |
| 5,817,626 A | 10/1998 | Findeis et al. ................ 514/12 |
| 5,817,879 A | 10/1998 | Hirschmann et al. ........ 568/333 |
| 5,821,231 A | 10/1998 | Arrhenius et al. ............ 514/18 |
| 5,827,647 A | 10/1998 | Young et al. |
| 5,874,529 A | 2/1999 | Gilon et al. ................. 530/317 |
| 5,916,563 A | 6/1999 | Young et al. |
| 6,001,371 A | 12/1999 | Young et al. |
| 6,132,732 A | 10/2000 | Young et al. |
| 6,204,044 B1 | 3/2001 | Brown |
| 6,274,307 B1 | 8/2001 | Soutschek et al. |
| 6,514,936 B1 * | 2/2003 | Greve et al. ..................... 514/8 |
| 6,551,597 B1 * | 4/2003 | Harrison et al. .......... 424/204.1 |

FOREIGN PATENT DOCUMENTS

| US | WO 99/18227 | * | 4/1999 |
| WO | WO 91/04330 A | | 4/1991 |
| WO | WO 91/12269 A1 | | 8/1991 |

OTHER PUBLICATIONS

Anderson and Young, *Monographs in Virology*, 20 (1997).
Armitage, "Emerging Applications of Recombinant Human . . . ," *Blood*, vol. 92, No. 12, pp. 4491–4508 (Dec. 15, 1998).
Benet, et al., "Pharmacokinetics: The Dynamics of Drug Absorption, Distribution, and Elimination," *The Pharmacological Basis of Therapeutics*, $8^{th}$ Ed., Goodman and Gilman's, pp. 3–32 (1990).
Bostic, et al., *J. Infect. Dis.*, 179:619 (1999).
Brown, et al., *J. Virol.*, 65:2702 (1991).
Brown, et al., *Science*, 262:114 (1993).
Burgess, et al., "Possible Dissociation of the Heparin–binding and Mitogenic Activities of . . . ," *The Journal of Cell Biology*, vol. 111, pp. 2129–2138 (11/90).
Chipman, et al., "Cryo–electron microscopy studies of empty capsids of human parvovirus B19 . . . ," *Proc. Natl. Acad. Sci. USA*, vol. 93, pp. 7502–7506 (07/96).
Cotmore, et al., *Science*, 226:1161 (1984).
Ek, et al., "Colony Formation of Human Fetal CD34+ Hematopoietic Cells," *Fetal Diagn. Ther.*, 11:326–334, 1996.
Ek, et al., "Cytokine Stimulation of Human Fetal Hematopoietic Cells," *Fetal Diagn. Ther.* 11:318–325, 1996.
Ek, "Effects of cryopreservation on subsets of fetal liver cells," *Bone Marrow Transplantation*, 11:395–398, 1993.
Ek, et al., "Immunological capacity of human fetal liver cells," *Bone Marrow Transplantation*, 14:9–14, 1994.
Erdman, et al., *J. Gen. Virol.*, 77:2767 (1996).
Farmer, et al., in TIPS, 9/82, pp. 362–365.
Fields, et al., *Virology*, vol. 2, $3^{rd}$ edition, Lippincott–Raven Pub., Philadelphia, PA, p. 2202, 2204, 2207 (1996).
Giralt, et al., *Blood*, 89:4531 (1997).
Jain, "Vascular and interstitial barriers to delivery of therapeutic agents in tumors," *Cancer Metastasis Rev.* 9(3):253–266, Nov. 1990.
Jain, "Delivery of Molecular Medicine to Solid Tumors," *Science*, vol. 271, pp. 1079–1080, Feb. 23, 1996.
Kajigaya, et al., *Proc. Natl. Acad. Sci. USA*, 86:7601 (1989).
Kajigaya, et al., *Proc. Natl. Acad. Sci. USA*, 88:4646 (1991).
Kaltenbronn, et al., *J. Med. Chem.*, 33:838–845 (1990).

(List continued on next page.)

*Primary Examiner*—James Housel
*Assistant Examiner*—Zachariah Lucas
(74) *Attorney, Agent, or Firm*—Knobbe Martens Olson & Bear, LLP

(57) ABSTRACT

The invention described herein relates to the discovery of methods and compositions for the inhibition of growth and/or migration of cells that have the P antigen, including but not limited to, cells of hematopoietic origin and endothelial cells. More specifically, parvovirus capsid particles or fragments of parvovirus capsid proteins are used to manufacture medicaments that can be administered to a subject to inhibit hematopoietic progenitor cell growth (e.g., prior to stem cell transplantation), endothelial cell growth, (e.g., as an anti-tumorigenesis treatment or to prevent restenosis or fibrotic build up following prosthetic implantation), or to prevent disorders that involve the abnormal proliferation of cells that have the P antigen (e.g., polycytemia vera).

8 Claims, 8 Drawing Sheets

OTHER PUBLICATIONS

Kemp, D.S., *Tibtech, "Peptidomimetics and the Template Approach to nucleation of beta–sheets and alpha–helics in Peptides"*, vol. 8, pp. 249–255 (1990).

Lazar, et al., *Molecular and Cellular Biology*, 8(3);1247–1252, Mar. 1988.

Le Blanc, et al., *European Journal of Haematology* 53:145–149, 1994.

Lindton, et al., "Mixed Lymphocyte Culture of Human Fetal Liver Cells," *Fetal Diagn. Ther.*, 15:71–78, 2000.

Lindton, et al., "Recombinant Parovirus B19 Empty Capsids Inhibit Fetal Hematopoietic Colony Formation in vitro," *Fetal Diagn. Ther.*, 16:26–31, 2001.

Liu, et al., "Interleukin–6 and the Granulocyte Colony-Stimulating Factor Receptor Are Major Independent Regulators . . . ," *Blood*, vol. 90, No. 7, pp. 2583–2590, Oct. 1, 1997.

Morey and Flemming, *Br. J. Hematol.*, 83:302 (1992).

Mortimer, et al., *Nature*, 302:426–429 (1983).

Ozawa, et al., *J. Virol.*, 62:2884 (1988).

Pabo, C.O., et al., *Biochemistry*, 25:5987–5991 (1988).

Perry, L.J. & Wetzel, R., Science, 226:555–557 (1984).

Rosenfeld, et al., *The Journal of Clinical Investigation*, 89:2023–2029, Jun. 1992.

Shields, et al., "In Vitro Hematopoiesis is Inhibited in Humans and non–human Primates by Recombinant Parvo Virus Capsid," 20th Annual Meeting of the Society for Maternal–Fetal Medicine, American Journal of Obstetrics and Gynecology, vol. 181, No. 1, part 2, Jan. 2002.

Slavin, et al., *Blood*, 91:756 (1998).

Verber, et al., in TINS, 9/85, pp. 392–396.

von dern Borne, et al., *Br. J. Hematol.*, 63:35–46 (1986).

Westgren, et al., *Am. J. Obstet. Gynecol.*, 176:49 (1996).

* cited by examiner

FIGURE 7

BacVP2

USE OF PAROVIRUS CAPSID PARTICLES IN THE INHIBITION OF CELL PROLIFERATION AND MIGRATION

CROSS REFERENCE TO RELATED APPLICATIONS

This application is a continuation of and claims priority to U.S. application Ser. No. 09/447,693, filed Nov. 23, 1999 now abandoned, which claims priority to Swedish Patent Application No. 9804022-3, filed Nov. 24, 1998, both of which are hereby expressly incorporated by reference in their entireties.

FIELD OF THE INVENTION

The present invention relates to the discovery of methods and compositions for the inhibition of cell growth and migration. More specifically, B19 parvovirus capsids or fragments of B19 parvovirus capsid proteins are used to manufacture medicaments that can be administered to a subject to inhibit the growth and/or migration of cells that have the P antigen, including, but not limited to, cells of hematopoietic origin and endothelial cells.

BACKGROUND OF THE INVENTION

The B19 parvovirus is a human pathogen that can be associated with various clinical conditions, ranging from mild symptoms (erythema infectiosum) to more serious diseases in persons who are immunocompromised or suffer from hemolytic anemias. Hydrops fetalis and intrauterine fetal death are well-known complications of B19 infection during pregnancy. (Anderson and Young, *Monographs in Virology,* 20 (1997)). The B19 parvovirus particles have icosohedral symmetry, a diameter of 18 to 26 nm, and are composed of 60 capsid proteins, approximately 95% of which are major capsid proteins (VP2) that have a molecular weight of 58 kd. (Fields et al., *Virology vol.* 2, 3rd edition, Lipponcott-Raven Publishers, Philidelphia, Pa., p. 2202 (1996)). Approximately, 3–5% of the capsid proteins that compose a B19 parvovirus capsid are called minor capsid proteins (VP1), which have a molecular weight of 83 kd, and differ from VP2 by an additional 227 amino acids at the amino terminus. (Id.).

The B19 parvovirus is extraordinarily tropic for human erythroid cells and cultures of bone marrow. B19 parvovirus binds to human erythroid progenitor cells, for example, and inhibits hematopoietic colony formation by replicating in these cells. (Brown et al., *Science,* 262:114 (1993) and Mortimer et al., *Nature,* 302:426 (1983)). The suppression of hematopoietic cells has also been seen in bone marrow samples from infected individuals, resulting in transient anemia and, in rare case, transient pancytopenia. (Saunders et al., *Br J Haematol,* 63:407 (1986)). Further, B19 parvovirus is known to cause bone marrow suppression in natural and experimental human infections. (Anderson and Young, *Monozraphs in Virology,* 20 (1997)).

The cellular receptor for B19 parvovirus has been identified as globoside or ertythrocyte P antigen, a textrahexoceramide. Fields et al., *Virology vol.* 2, 3rd edition, Lipponcott-Raven Publishers, Philidelphia, Pa., p. 2204 (1996)). The P antigen is found on mature erythrocytes, erythroid progenitors, megakaryocytes, endothelium, kidney cortex, placenta, fetal myocardium (von dem Bome et al., *Br J Hematol,* 63:35 (1986)) and pronormoblasts from fetal liver. (Morey and Flemming, *Br J Haematol,* 82:302 (1992)). Individuals who genetically lack the P antigen are not susceptible to B19 parvovirus infection and administration of either excess P antigen or monoclonal antibodies directed to the P antigen can protect erythroid progenitors from infection with B19 parvovirus. (Id.).

Additionally, neutralizing antibodies that recognize several regions of the B19 parvovirus particle have been generated. For example, monoclonal antibodies directed to epitopes of VP2, such as found at amino acids 38–87, 253–272, 309–330, 328–344, 359–382, 449–468, and 491–515, and the unique region of VP1 can neutralize B19 parvovirus. (Fields et al., *Virology vol.* 2, 3rd edition, Lipponcott-Raven Publishers, Philidelphia, Pa., p. 2207 (1996)).

Genetically engineered expression systems for the production of B19 parvovirus antigens have also been developed. (Kajigaya et al., *Proc Natl Acad Sci USA,* 86:7601 (1989); Kajigaya et al., *Proc Natl Acad Sci USA,* 88:4646 (1991); Brown et al., *J Virol,* 65:2702 (1991)). Like the native particles, recombinant B19 parvovirus capsids, produced in a baculovirus system, are composed of both VP1 and VP2 and these capsid proteins self assemble to form virus-like particles (VLPs). (Kajigaya et al., *Proc Natl Acad Sci USA,* 88:4646 (1991)). Electron microscopic analyses of the B19 parvovirus capsids revealed that the VLPs are structurally similar to plasma-derived virions. (Kajigaya et al., *Proc Natl Acad Sci USA,* 88:4646 (1991)). B19 VLPs are currently being evaluated as a potential vaccine against B19 parvovirus infection and preliminary results show a good neutralizing response without severe side effects. (Bostic et al, *J Infect. Dis.,* 179:619 (1999). While many are trying to prevent B19 parvovirus infection by administering B19 capsids, none have sought to exploit the properties of the B19 parvovirus capsid, B19 capsid proteins, or fragments thereof to develop novel medicaments that inhibit cell proliferation or migration.

BRIEF SUMMARY OF THE INVENTION

In the invention described herein, the inventors disclose the discovery that the B19 parvovirus capsid, B19 parvovirus capsid proteins, or fragments thereof inhibit the growth and/or migration of cells that have the P antigen. Embodiments of the invention include medicaments comprising B19 parvovirus capsid, B19 parvovirus capsid proteins, or fragments thereof that can be administered to subjects in need of an agent that inhibits cell growth and/or migration. Methods of treatment of diseases or conditions associated with hematopoietic or endothelial cell proliferation or migration are also within the scope of aspects of the invention.

One embodiment, for example, involves the use of empty, noninfectious, recombinant B19 parvovirus capsids, B19 capsid proteins, or fragments of B19 capsid proteins for the production of a medicament for the inhibition of growth or migration of cells that have the P antigen. The medicament, according to this use, can be for the inhibition of hematopoietic cell growth, endothelial cell growth, or endothelial cell migration. Additionally, the medicament according to this use can be for the treatment of hematological proliferative disorders, angiogenesis, tumorigenesis, or endothelial cell ingrowth into an implanted prosthetic device. Further, the medicament according to this use can be for treatment of a subject prior to stem cell transplantation and the subject can be a fetus.

In another embodiment, a method of inhibiting the growth or migration of a cell having the P antigen is provided. This method comprises the steps of contacting a cell with a capsid agent selected from the group consisting of B19 parvovirus capsid, B19 capsid protein, and a fragment of a B19 capsid protein and measuring the inhibition of cell growth or cell migration. In some aspects, the cell can be a cell of hematopoietic origin or an endothelial cell.

A method of treating a subject prior to stem cell transplantation is also embodied in the invention. This method is performed by identifying a subject in need of a capsid agent that inhibits hematopoietic cell growth and providing said subject in need with an effective amount of capsid agent selected from the group consisting of B19 parvovirus capsid, B19 capsid protein, and a fragment of a B19 capsid protein. Similarly, a related embodiment, concerns a method of treating a subject for a hematopoietic proliferative disorder comprising the steps of identifying a subject in need of a capsid agent that inhibits a hematopoietic proliferative disorder and providing said subject in need with an effective amount of capsid agent selected from the group consisting of B19 parvovirus capsid, B19 capsid protein, and a fragment of a B19 capsid protein.

A method of inhibiting tissue ingrowth into an implanted prosthesis is also provided. This approach comprises the steps of identifying a subject in need of a capsid agent that inhibits tissue ingrowth into an implanted prosthesis and providing said subject in need with an effective amount of capsid agent selected from the group consisting of B19 parvovirus capsid, B19 capsid protein, and a fragment of a B19 capsid protein. Another embodiment involves a method of treating or preventing tumorigenesis and this method comprises the steps of identifying a subject in need of a capsid agent that inhibits hematopoietic cell growth and providing said subject in need with an effective amount of capsid agent selected from the group consisting of B19 parvovirus capsid, B19 capsid protein, and a fragment of a B19 capsid protein.

A kit having a capsid agent is also an embodiment and one such kits comprises a capsid agent selected from the group consisting of B19 parvovirus capsid, B19 capsid protein, and a fragment of a B19 capsid protein and instructions for dosage and administration to a subject for hematopoietic progenitor cell growth inhibition, hematopoietic progenitor cell growth inhibition, endothelial cell growth inhibition or treatment of a hematological proliferative.

BRIEF DESCRIPTION OF THE DRAWINGS

Figure 7:
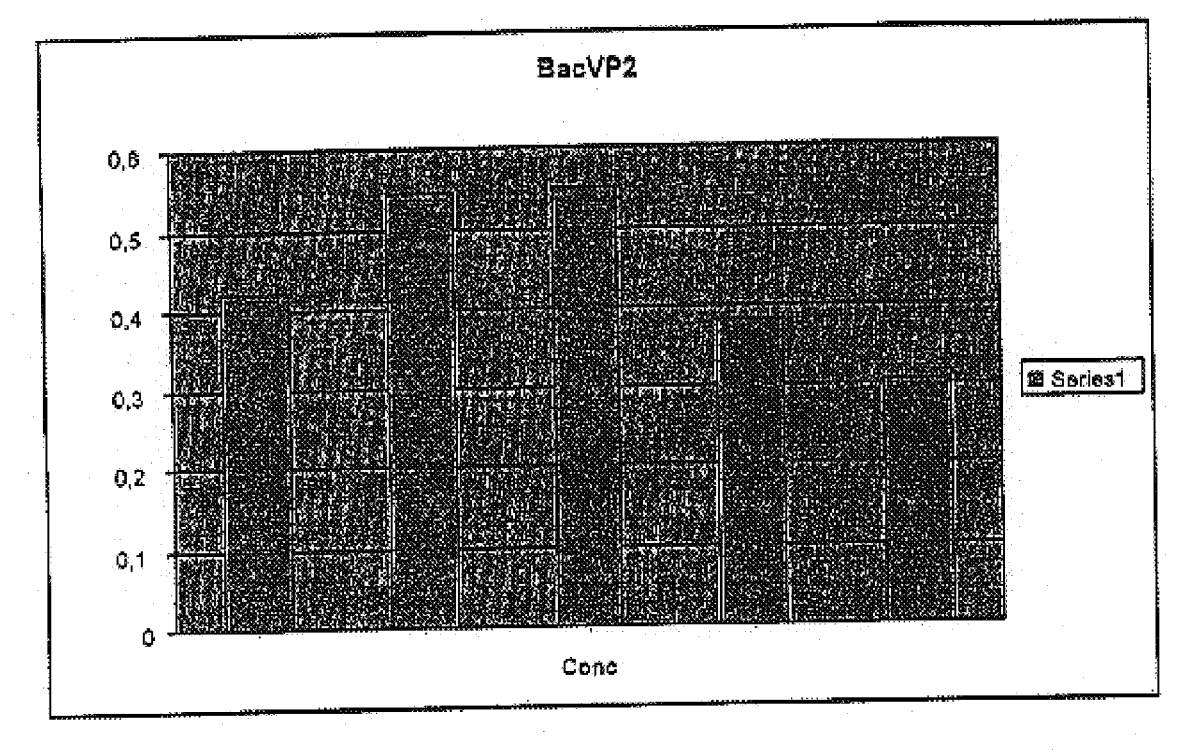

FIG. 7 This figure shows a bar graph that represents the results of cell proliferation assays performed on human umbilical vein endothelial cells (HUVEC) that were contacted with varying concentrations of B19 parvovirus capsid (VP2). On the "x axis" are increasing concentrations of B19 parvovirus capsid (VP2) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

DETAILED DESCRIPTION OF THE INVENTION

Figure 1:
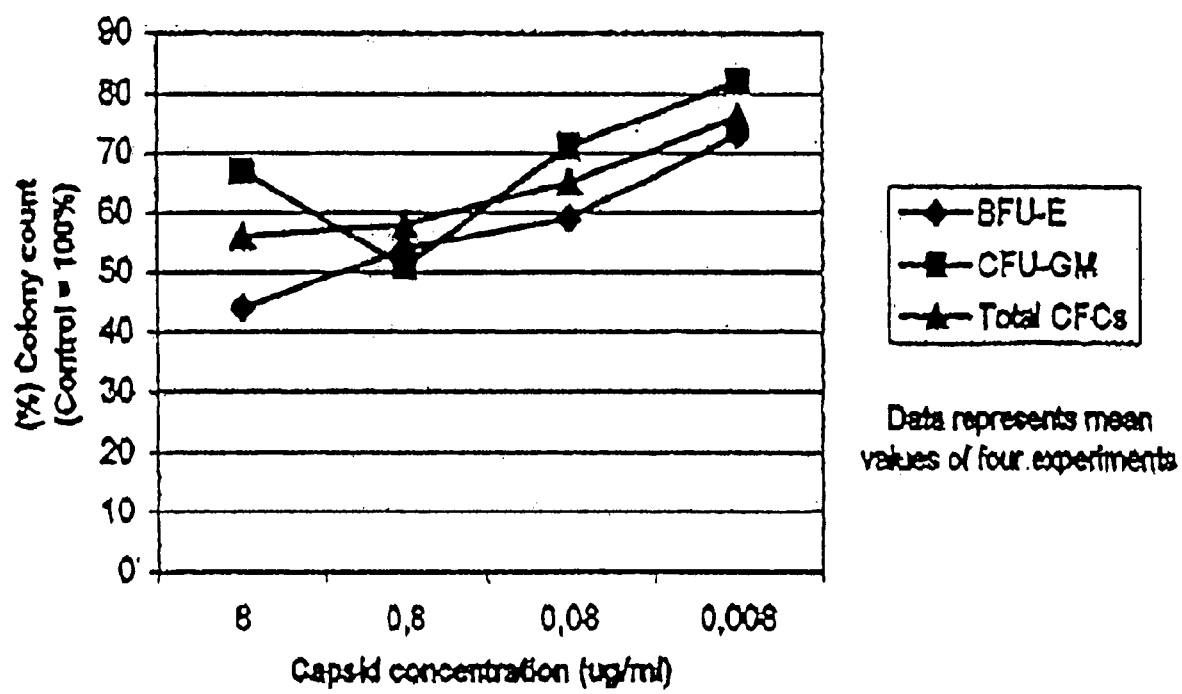
FIG. 1 This figure shows a graphical representation of the results of colony formation assays performed on cells from human cord blood that were contacted with varying concentrations of B19 parvovirus capsids (VP1/2).

In the invention described herein, the inventors disclose the discovery that the B19 parvovirus capsid, B19 parvovirus capsid proteins, or fragments thereof inhibit the growth and/or migration of cells that have the P antigen. By using colony formation assays, the inventors demonstrate that B19 parvovirus capsids composed of VP1 and VP2 or just VP2 alone can inhibit the growth of several different types of cells of hematopoietic origin including human fetal liver cells, human umbilical cord blood cells, and adult bone marrow cells. Additionally, the inventors have discovered that B19 parvovirus capsids inhibit the growth of bone marrow cells obtained from Baboons and Macaques. Further, through the use of neutralization assays using monoclonal antibodies directed to the P antigen, monoclonal antibodies known to inhibit B19 parvovirus infection, and B19 IgG positive sera obtained from two asymptomatic individuals, the inventors show that the B19 parvovirus capsids inhibit hematopoietic cell growth through an interaction involving the P antigen. Additionally, the inventors found that the B19 parvovirus capsids were internalized in cells that have the P antigen by immunolabeling the B19 parvovirus capsids after incubation with cells that have the P antigen.

The inventors have also discovered that B19 parvovirus capsids inhibit the proliferation and migration of endothelial cells. Endothelial cell proliferation assays were performed by contacting human umbilical vein endothelial cells (HUVEC) with fibroblast growth factor in the presence of B19 parvovirus capsids. Cell proliferation was monitored by crystal violet staining and the results established that B19 parvovirus capsids effectively reduced endothelial cell proliferation. By using a Boyden chamber assay, the inventors further demonstrated that B19 parvovirus capsids inhibited the migration of HUVEC cells.

Several embodiments of the invention involve the manufacture of modified B19 parvovirus capsids. The inventors disclose many approaches to manufacture B19 parvovirus capsids having less than 5% VP1 and B19 parvovirus capsids having only VP2. Further, the inventors teach the manufacture of fragments of the B19 capsid proteins, and peptidomimetics resembling these peptides, that can be used to inhibit the growth and or migration of cells that have the P antigen. The peptide fragments of the invention can be at least 3 amino acids in length up to 780 amino acids in length and can comprise conservative amino acid substitutions. Additionally, the B19 parvovirus capsids, B19 capsid proteins, or fragments of B19 capsid proteins can be modified by the inclusion of substituents that are not naturally found on the B19 capsid proteins, the inclusion of mutations, or through the creation of fusion proteins. Derivatized or synthetic B19 capsid proteins are also embodiments. Further, the inventors teach approaches to design and manufacture B19 parvovirus capsids, B19 capsid proteins, or fragments of B19 capsid proteins that induce a minimal immune response in a subject so as to allow for the long-term treatment protocols. Still further, the inventors describe the construction of profiles on the various B19 capsid-based therapeutics, which includes information such as sequences, sites of mutations or modifications, performance information in functional assays, and therapeutic information including disease indications, clinical evaluations and the like.

Other embodiments of the invention include the preparation of multimeric displays of B19 parvovirus capsids, B19 capsid proteins, or fragments of B19 capsid proteins. These multimeric agents are created by joining B19 parvovirus capsids, B19 capsid proteins, or fragments of B19 capsid proteins to a support, which can be a bead, a resin, a plastic dish, and, preferably, a medical device, such as a stent, valve, or other prosthetic. Advantageously, these multimeric displays can provide a potent agent that inhibits the proliferation and/or migration of cells that have the P antigen (e.g., restenosis following implantation). The inventors also teach the preparation of many different pharmaceuticals and medical devices that comprise B19 parvovirus capsids, B19 capsid proteins, or fragments of B19 capsid proteins. These pharmaceuticals can be formulated with other additives, carriers, or excipients so as to allow administration by many routes.

Therapeutic and prophylactic methods are also within the scope of the invention. In several embodiments, the inventors teach ways to inhibit the proliferation and/or migration of cells that have the P antigen, including, but not limited to cells of hematopoietic origin and endothelial cells, by administering a therapeutic comprising B19 parvovirus capsids, B19 capsid proteins, or fragments of B19 capsid proteins. In one aspect, a method to inhibit hematopoiesis in a subject prior to in utero stem cell transplantation is provided. In a related method, the inventors teach an approach to inhibit hematopoiesis in a subject prior to post natal stem cell transplantation (e.g., a novel approach to non-myeloblative therapy). Other methods of the invention include an approach to inhibit cell proliferation in a subject suffering from an hematological proliferative disorder, such as Polycythemia Vera. Still further, are embodiments that include methods of preventing angiogenesis, tumorigenesis, or cancer and methods of preparing medical devices, such as stents or valves, that prevent fibrotic build up or restenosis or otherwise delay endothelial cell ingrowth. Kits comprising B19 parvovirus capsids, B19 capsid proteins, or fragments of B19 capsid proteins are also embodiments of the invention. In the section below, the inventors describe experiments that provide evidence that B19 parvovirus capsids inhibit the growth of hematopoietic cells.

B19 Parvovirus Capsids Inhibit the Growth of Hematpoietic Cells

In a first set of experiments, the inventors discovered that recombinant B19 parvovirus capsids can be used to inhibit hematopoietic cell growth, as evidenced by a reduction in colony formation of fresh human fetal liver cells, umbilical cord blood cells, and bone marrow cells. A description of these experiments is provided below.

To obtain fetal liver tissue, human fetuses 6–12 weeks of gestational age were obtained from legal abortions; the patients had volunteered to donate fetal tissue. Gestational age was estimated according to specific anatomical markers and is given as menstruational age. Abortions were performed with vacuum aspirations. Fetal liver was dissected under sterile conditions, placed in a sterile tube containing RPMI1640 and disintegrated by passage through a vinyl mesh to form a single cell suspension. Nucleated cells were then washed three times, counted and diluted in culture medium.

A commercial kit—the "Stem cell CFU kit" (GIBCO BRL, Life Technology Inc., NY, USA)—was used to perform colony formation assays. The kit provides a semi-solid support that mimics the extracellular matrix produced by stromal cells. Other components included in the kit are: Iscove's modified Dulbecco's medium, modified fetal bovine serun, methylcellulose, 2-mercaptoethanol, conditioned medium and erythropoietin. The colonies that formed were identified as BFU-E (burst forming unit-erythroid cells) with densely packed hemoglobonized cells, CFU-GM (colony forming units-granulocytes, macrophages) with arrangements of non-hemoglobinized cells, and CFU-GEMM (colony forming units-granulocytes, erythroid cells, macrophages, megakaryocytes) with hemoglobinized cells and small and large peripheral cells.

Recombinant parvovirus B19 empty capsid particles (Kajigaya et al., *Proc Natl Acad Sci USA,* 88:4646 (1991)) were a gift from MedImmune (Gaithersburg, Md., USA) and were prepared in a recombinant baculovirus-insect cell (*Spodofera frugiperda*) expression system. (Kajigaya et al., *Proc Natl Acad Sci USA,* 88:4646 (1991)). The capsids were diluted in buffer (20 mM Tris, 0.5M NaCl, pH 8.5) and 30 $\mu$L of each dilution was added to $25\times10^3$ cells ($50\times10^3$ for postnatal cells) in 100 $\mu$L of culture medium and incubated for 1 hr in +4 ° C. The mixtures were then transferred to incubation dishes and culture medium was added to a final volume of 0.5 ml per well. The cells were incubated for 11 days in a humidified atmosphere at 5% $CO_2$, and were then scored for BFU-E, CFU-E and CFU-GEMM derived colony formation in the colony formation assay.

In the 11-day colony formation assay, the inventors found that B19 parvovirus capsids inhibited hematopoietic cell growth, as evidenced by a reduction in colony formation of fresh human fetal liver cells, umbilical cord blood cells, and adult bone marrow cells. That is, a reduction in colony formation of BFU-E (burst forming unit-erythroid), CFU- GM (colony forming unit-granulocyte, macrophage) and CFU-GEMM (colony forming unit-granulocyte, erythrocyte, monocyte, megakaryocyte) cells was observed when human fetal liver cells, umbilical cord blood cells, and adult bone marrow cells were incubated with B19 parvovirus capsids. (See Table 1).

TABLE 1

Colony-forming unit assay of fetal liver cells*.

| Dilution of Parvovirus B19 capsid (µg/ml) | Colony Counts (% of medium control) | | |
| --- | --- | --- | --- |
| | BFU-E | CFU-GM | CFU-GEMM |
| 70.0 | 22% | 14% | 31% |
| 0.7 | 39% | 54% | 63% |
| 0.007 | 79% | 95% | 94% |
| Medium (=100%), counts | 95 | 37 | 16 |

*The cells were pre-incubated with dilutions of the parvovirus B19 capsids prior to the 11 day culture.

As shown in Table 1, an inhibition of hematopoietic cell growth was seen with as little as 0.007 µg/ml B19 parvovirus capsid and considerable inhibition of hematopoietic cell growth was observed at 70.0 µg/ml B19 parvovirus capsid.

Recombinant papillomavirus capsids (Cottontail rabbit papillomavirus and human papillomavirus type 6) were included in the colony formation assays as controls. These capsids are structurally similar to parvovirus B19 capsids but do not interact with the P antigen. Recombinant human papilloma virus capsids (HPV6) and Cottontail rabbit papillomavirus (CRPV) capsids were gifts from Dr. J. Dillner, Karolinska Institute, Stockholm, Sweden. Whereas the parvovirus B19 capsids inhibited hematopoietic cell growth, the papilloma virus capsids (tested in the range 0.01–100 μg/ml) had no effect on colony formation.

In a second set of experiments, the inventors found that the colony formation of hematopoietic cells could be rescued by incubating parvovirus B19 capsids with anti-B19 monoclonal antibodies or with parvovirus B19 IgG positive human sera, prior to adding the mixture to the cells. The anti-parvovirus B19 monoclonal antibody (MAB8292), which is an IgG class antibody, was purchased (Cehmicon AB, Malmo, Sweden) and the Parvovirus B19 IgG positive (parvovirus B19 IgM negative) sera were obtained from two asymptomatic individuals. In one neutralization experiment, parvovirus B19 capsids were incubated with anti-B19 monoclonal antibody (MAB8292) prior to adding the mixture to fetal liver cells. Approximately, 25 μl of anti-parvovirus B19 monoclonal antibody (MAB8292) was incubated with 25 μl of parvovirus B19 capsids for 2 hours at +4° C. The mixtures were then added to the cells and the 11-day colony formation assay, as described above, was performed on the "neutralized"—capsid/cell mixture.

Although a relatively high concentration of parvovirus B19 capsids was used (7 μg/ml, as compared to the values in Table 1), as little as 0.02 μg/ml of the anti-B19 monoclonal antibody reduced the ability of parvovirus B19 capsids to inhibit fetal liver cell growth and a concentration of 20.0 μg/ml of the anti-B19 monoclonal antibody completely blocked the inhibition on BFU-E colony formation and drastically reduced the effect on CFU-GM and CFU-GEMM colony formation (See Table 2).

TABLE 2

Neutralization assay using anti-parvovirus B19 monoclonal antibody*.

| Parvovirus B19 capsid (7 μg/ml) + dilutions of Anti-parvovirus B19 Mab (μg/mL) | Colony Counts (% of medium control) BFU-E | CFU-GM | CFU-GEMM |
|---|---|---|---|
| 20.0 | >100% | 74% | 67% |
| 2.0 | 69% | 35% | 45% |
| 0.2 | 52% | 21% | 19% |
| 0.02 | 52% | 30% | 21% |
| capsid only | 43% | 30% | 21% |
| Medium (=100%), counts | 114 | 66 | 42 |

*The cells were pre-incubated with the reagents prior to the 11 day culture.

Similarly, the two lots of parvovirus B19 IgG positive sera were analyzed for their ability to neutralize the B19 parvovirus capsids. Approximately, 25 μl of parvovirus B19 IgG positive serun was incubated with 25 μl of parvovirus B19 capsids for 2 hours at +4° C., then the mixtures were added to fetal liver cells. Subsequently, the colony formation assay described above was performed on the sera-neutralized B19 capsid/cell mixture. As shown in Table 3, in the absence of sera, parvovirus B19 capsids (0.14 μg/ml) significantly inhibited fetal liver cell colony formation, whereas, as little as a 1:100 dilution of serum 1 reduced the ability of parvovirus B19 capsids to inhibit fetal liver cell growth.

TABLE 3

Neutralization assay using human parvovirus B19 IgG positive sera*.

| Parvovirus B19 capsid (0.14 μg/ml) + dilutions of two human parvovirus B19 IgG positive sera | Colony Counts (% of medium control) BFU-E | CFU-GM | CFU-GEMM |
|---|---|---|---|
| Serum 1, 1:10 | 70% | 78% | 90% |
| Serum 1, 1:100 | 25% | 23% | 40% |
| Serum 2, 1:10 | 48% | 57% | 57% |
| Serum 2, 1:100 | 17% | 27% | 67% |
| capsid only | 18% | 17% | 63% |
| Medium (=100%), counts | 157 | 81 | 30 |

*The cells were pre-incubated with the reagents prior to the 11 day culture.

Further evidence that parvovirus B19 capsids inhibit the growth of hematopoietic cells was obtained by performing neutralization assays using monoclonal antibodies directed to the P-antigen. The anti-P monoclonal antibody (CLB-ery-2), a mouse IgM class antibody, was a gift from Dr. de Jong and Dr. von dem Borne (Central Laboratory of the Netherlands Red Cross Blood Transfusion Service, Amsterdam, The Netherlands). (See von dem Bome et al., *Br J Hematol,* 63:35 (1986)). In these assays, approximately $2.5\times10^4$ fetal liver cells were suspended in 100 μl of medium and were then incubated with either 25 μl of anti-P monoclonal antibody (CLB-ery-2) or 25 μl of anti-$P_1$ (Seraclone), a control monoclonal antibody. Cells and monoclonal antibody were incubated for 1 hr at 4° C. The cell/antibody mixtures were washed twice in cold culture medium prior to adding the parvovirus B19 capsids and, subsequently, the colony formation assays were conducted, as previously described.

In accord with the evidence from the previous experiments and studies conducted with native viral particles (See Brown et al., *Science,* 262:114 (1993)), the inventors discovered that the monoclonal antibodies directed to the P antigen could restore growth of fresh fetal liver cells incubated in the presence of parvovirus B19 capsids. As shown in Table 4, the inhibitory effect of the parvovirus B19 capsid was reduced by at least 25% when the cells were incubated in the presence of CLB-ery-2. In contrast, the anti-$P_1$ (Seraclone) monoclonal antibody (Labdesign, Stockholm, Sweden), which does not interact with the P antigen, had no effect on colony formation as compared to the parvovirus B19 capsid control.

TABLE 4

Neutralization assay using anti-P or AntiP$_1$ monoclonal antibodies*

| | Colony Counts (% of medium control) | | |
|---|---|---|---|
| | BFU-E | CFU-GM | CFU-GEMM |
| Parvovirus B19 capsid (0.14 µg/ml) + of Anti-P Mab (titer) | | | |
| 1:5 | 51% | 39% | 93% |
| 1:500 | 23% | 10% | 43% |
| capsid only | 18% | 17% | 63% |
| Medium (=100%), counts | 157 | 81 | 30 |
| Parvovirus B19 capsid (0.14 µg/mL) + of Anti-P$_1$ Mab (µg/ml) | | | |
| 400.0 | 25% | 20% | 50% |
| 4.0 | 17% | 22% | 47% |
| capsid only | 18% | 17% | 63% |
| Medium (=100%), counts | 157 | 81 | 30 |

*The cells were pre-incubated with the reagents prior to the 11 day culture.

The inhibitory effect of parvovirus B19 capsids on colony formation was also tested using fresh stem cells derived from cord blood and adult bone marrow samples. Colony formation assays in the presence of B19 parvovirus capsids were performed on cells obtained from umbilical cord blood and bone marrow using the protocol described above. Umbilical cord blood samples were obtained immediately after vaginal delivery from normal births. Samples of adult bone marrow were obtained from healthy allogeneic donors. Suspensions of fresh cells were heparinized and diluted in 0.9% NaCl and separated on Lymphoprep (Nycomed, Parma, Oslo, Norway) for gradient centrifugation at 2000 rpm for 20 min. Cells were carefully removed with a Pasteur pipette, washed three times in 0.9% NaCl, counted and diluted in culture medium in preparation for the colony formation assays.

The ability of parvovirus B19 capsids to inhibit hematopoietic cells obtained from cord blood and bone marrow was comparable to that exhibited with fetal liver cells (See Table 5). As shown in FIG. 1, for example, the growth of cells obtained from human cord blood decreased as the. concentration of parvovirus B19 capsid increased. Further, neutralization assays using cells obtained from cord blood or bone marrow and parvovirus B19 capsids also exhibited results similar to those seen with human fetal liver cells. That is, parvovirus B19 capsids that were incubated with the anti-parvovirus B19 monoclonal antibody (Mab8292) prior to contact with the cells obtained from cord blood and bone marrow demonstrated a reduced ability to inhibit cell growth, as evidenced by an increase in colony formation.

TABLE 5

Colony formation assay on cord blood and adult bone marrow cells

| | Colony Counts (% of medium control) | | |
|---|---|---|---|
| | BFU-E | CFU-GM | CFU-GEMM |
| Parvovirus B19 capsid (µg/ml) Cord blood cells | | | |
| 7.0 | 10% | 54% | 43% |
| 0.7 | 33% | 62% | 43% |
| 0.07 | 49% | 72% | 50% |
| 0.007 | 57% | 67% | 70% |
| 0.0007 | 84% | 79% | 93% |
| Medium (=100%), counts | 134 | 39 | 30 |
| Bone marrow cells | | | |
| 7.0 | 18% | 36% | 6% |
| 0.7 | 43% | 45% | 28% |
| 0.07 | 63% | 41% | 44% |
| 0.007 | 76% | 80% | 78% |
| 0.0007 | 86% | 77% | 78% |
| Medium (=100%), counts | 134 | 39 | 30 |

*The cells were incubated with dilutions of B19 capsid (µg/mL) prior to the 11 day culture.

Figure 2:
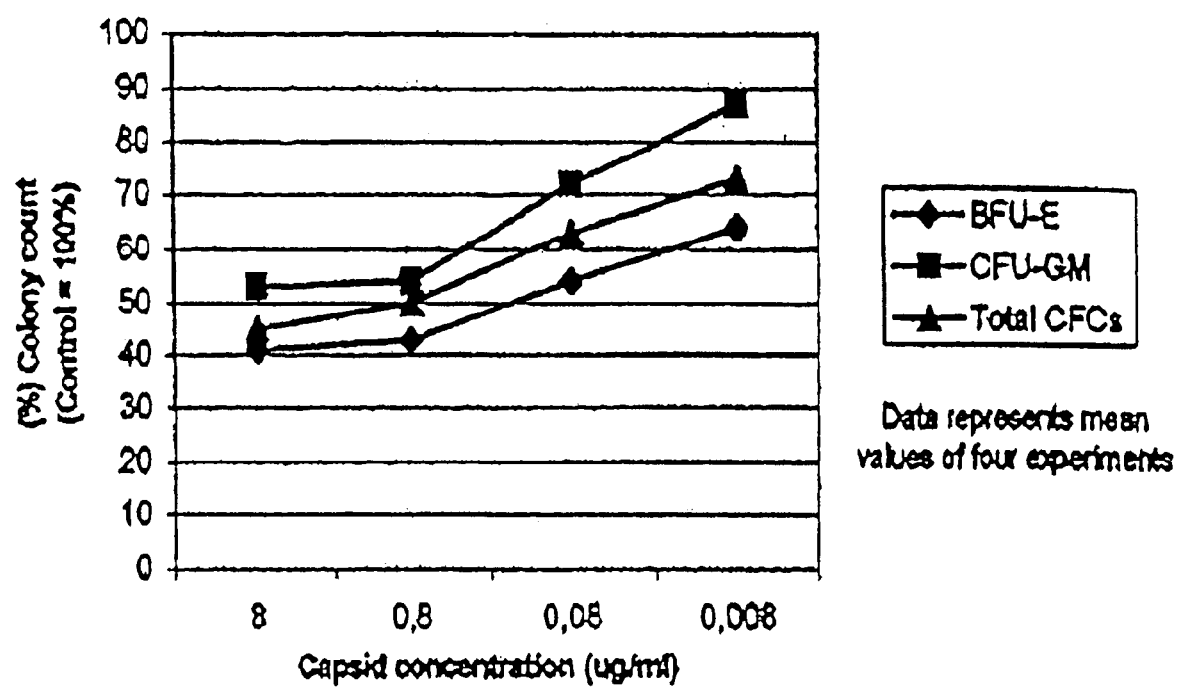
FIG. 2 This figure shows a graphical representation of the results of colony formation assays performed on cells from monkey (Baboon and Macaque) bone marrow that were contacted with varying concentrations of B19 parvovirus capsids (VP1/2).
Figure 3:
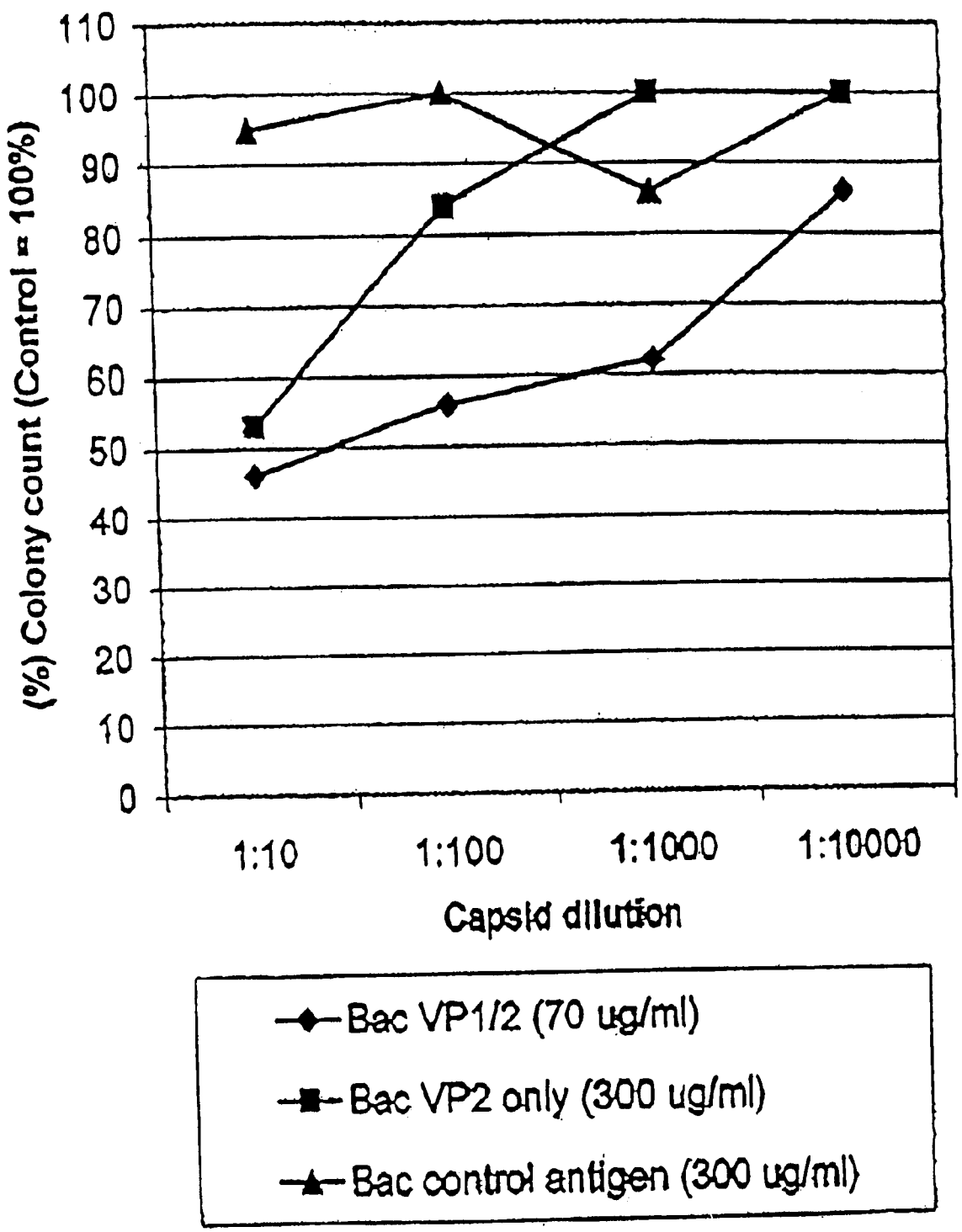
FIG. 3 This figure shows a graphical representation of the results of colony formation assays performed on cells from human fetal liver that were contacted with varying concentrations of B19 parvovirus capsids (BacVP1/2), B19 parvovirus capsids having only VP2 (Bac VP2 only), or a control antigen (Bac control antigen).
Figure 4:
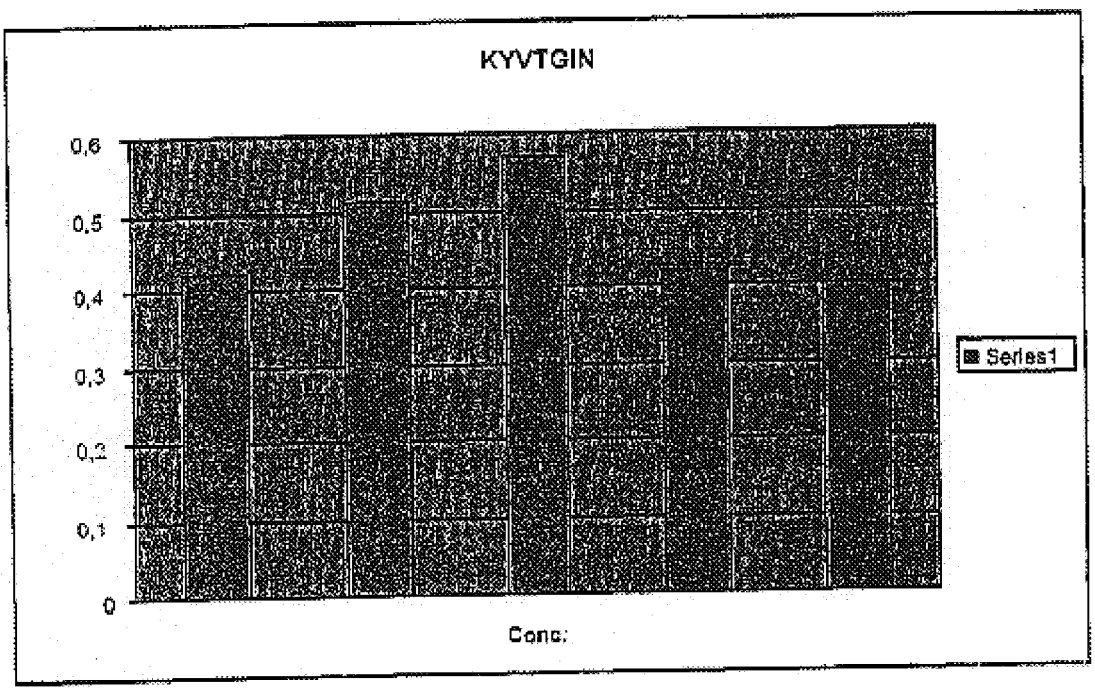
FIG. 4 This figure shows a bar graph that represents the results of cell proliferation assays performed on human umbilical vein endothelial cells (HUVEC) that were contacted with varying concentrations of a control antigen (KYVTGIN) (SEQ. ID. NO. 1). On the "x axis" are increasing concentrations of the control antigen (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).
Figure 5:
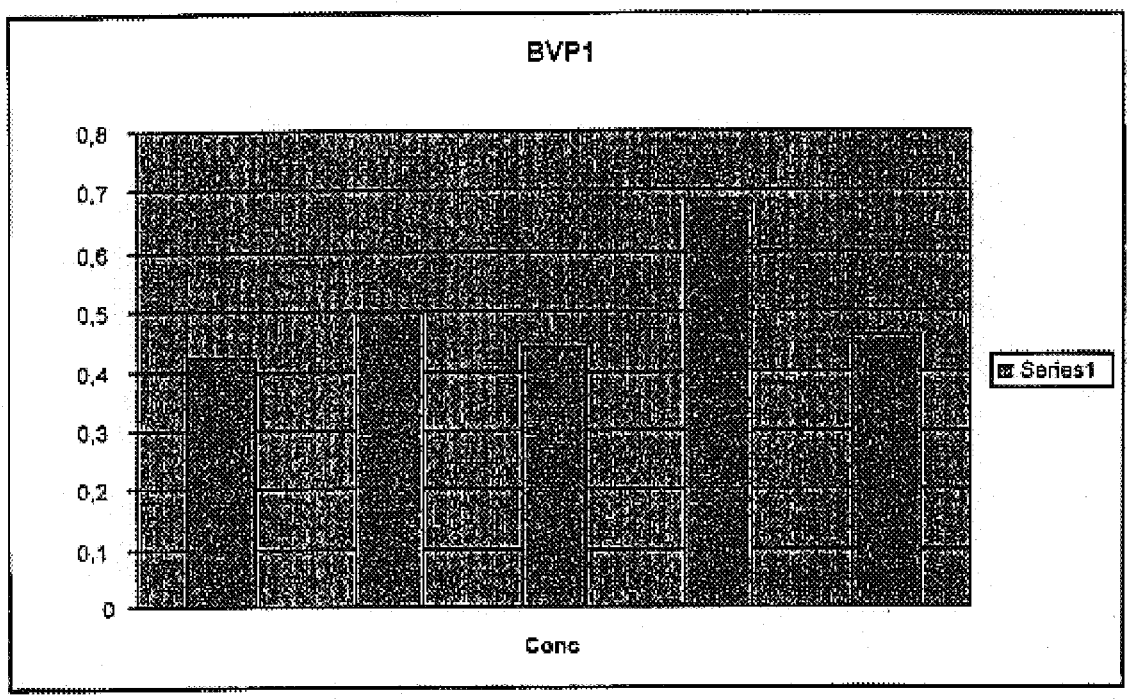
FIG. 5 This figure shows a bar graph that represents the results of cell proliferation assays performed on human umbilical vein endothelial cells (HUVEC) that were contacted with varying concentrations of B19 parvovirus capsids composed of only VP1. On the "x axis" are increasing concentrations of the B19 parvovirus capsid (VP1) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).
Figure 6:
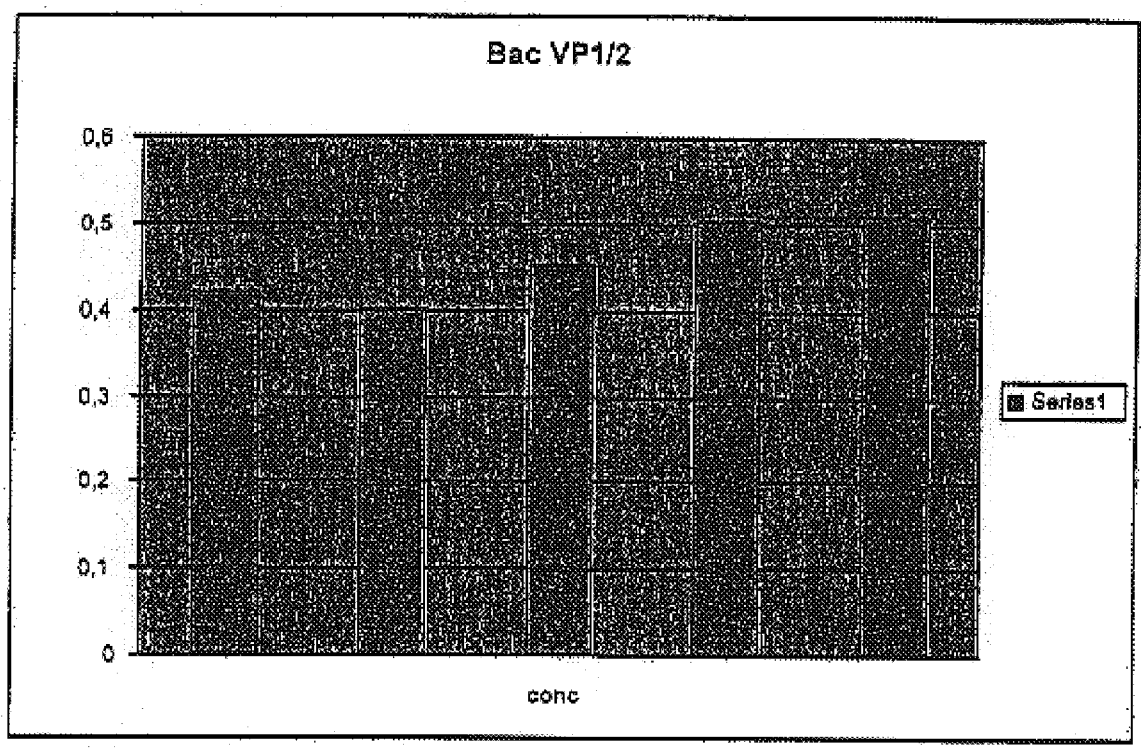
FIG. 6 This figure shows a bar graph that represents the results of cell proliferation assays performed on human umbilical vein endothelial cells (HUVEC) that were contacted with varying concentrations of B19 parvovirus capsid (VP1/2). On the "x axis" are increasing concentrations of B19 parvovirus capsid (VP1/2) (from left to right), 0 $\mu$g/ml, 0.01 $\mu$g/ml, 0.1 $\mu$g/ml, 1.0 $\mu$g/ml, and 10.0 $\mu$g/ml. On the "y axis" are shown spectrophotometric absorbance values taken at 540 nm ($A_{540}$).

Additionally, colony formation assays in the presence of parvovirus B19 cells were performed, as described above, using hematopoietic cells obtained from the bone marrow of monkeys (Baboons and Macaques). As shown in FIG. 2, primate hematopoietic cell growth decreased in concordance with an increase in concentration of parvovirus B19 capsid. The results from this experiment not only demonstrate that primate hematopoietic cells have a P antigen that interacts with parvovirus B19 capsids but also established that the Baboon and Macaque is suitable for in vivo study of the therapeutic and prophylactic embodiments of the invention. In the next section, the inventors describe the discovery that modified B19 parvovirus capsids and peptides that compose B19 parvovirus capsids can be used to inhibit hematopoietic cell growth.

Modified B19 Parvovirus Capsids and Peptides that Compose B19 Parvovirus Capsids Inhibit Hematopoietic Cell Growth In this section, the inventors describe how to make modified B19 capsids that have different proportions of VP1 and VP2 proteins or VP2 alone, which can be used in long-term treatment protocols to inhibit hematopoietic cell growth. In an effort to identify the regions of the B19 parvovirus capsid that are involved in inhibiting cell growth, the inventors discovered that after binding of the P antigen, the capsid fuses with cells having the P antigen and becomes internalized. In one experiment that provided evidence of B19 parvovirus capsid internalization, the inventors incubated fetal liver cells with B19 parvovirus capsids and the capsid treated cells were fixed on BioRad slides, labeled with the anti-B19 monoclonal antibody (Mab8292), and detected with a fluorescent secondary antibody. Accordingly, fetal liver cells were washed in PBS and a suspension with a concentration of $2\times10^6$/ml was prepared. A fraction of the suspension was incubated with B19 native capsid, (0.35 μg capsid/ml cell susp.), in 37° C. for 1 hour. Approximately, 20 μl droplets (about 40,000 cells) of cell/capsid suspension was then placed on two BioRad slides, 10 wells on each slide. In two of the wells on each slide, cells that had not been treated with capsids were used as controls. Next, the cells on one of the two BioRad® slides were perrmeablized with saponine, which permits antibody penetration. Subsequently, primary anti-B19 monoclonal IgG antibody was added and, after binding and removal of unbound primary antibody with a PBS wash, the secondary fluorescent anti-IgG antibody was added, allowed to bind, and the unbound secondary was removed with a PBS wash. A UV-light microscope was used for the analysis. Saponin permeablized cells treated with B19 parvovirus capsids exhibited fluorescence on cell membranes and inside the cells. In contrast, control cells, which were not permeablized with saponin, exhibited fluorescence only at the cell surface. These results provide evidence that the inhibition of cell growth mediated by the B19 parvovirus capsid can involve more than protein sequences that encode the receptor for the P antigen.

Although embodiments of the invention can comprise B19 parvovirus capsids without modification, native B19 VLPs (i.e., capsids having 95% VP2 and 5% VP1) elicit an immune response, which makes them less desirable for some therapeutic applications (e.g., use in long term treatment protocols). Others have constructed a modified B19 parvovirus capsid having 25% VP1 and 75% VP2 while trying to develop a parvovirus vaccine, however, this modified VLP induces an elevated neutralizing response in vivo. (See U.S. Pat. No. 5,508,186 to Young et al.). Such modified B19 parvovirus capsids are undesirable for long-term therapeutic protocols because a subject's immune response can quickly clear the VLPs from the subject's body, thus, lowering the effective dose. Additionally, since the prevalence of antibodies to parvovirus in the population approaches 50%, it is preferred that treatment protocols use capsid agents that elicit a minimal immune response. Since the unique region of VP1 appears to play an integral role in immune response to the B19 parvovirus capsid (See Fields et al., *Virology vol.* 2, 3rd edition, Lipponcott-Raven Publishers, Philidelphia, Pa., p. 2207 (1996)), modified capsids that comprise less VP1 than is found in nature can be manufactured and can be more effective therapeutics for long term use. That is, some embodiments include B19 parvovirus capsids that comprise an amount of VP1 that is less than or equal to 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.2%, 2.3%, 2.4%, 2.5%, 2.6%, 2.7, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of the total amount of VP1 and VP2. The B19 parvovirus capsids (VP1 alone and VP1/2) were obtained from Klaus Heddman from the University of Helsinki, Finland.

Further, recombinant VP2 can spontaneously form capsid structures that are similar to the VP1/VP2 structure without VP1. (See U.S. Pat. No. 5,508,186 to Young et al.). The VP2 capsids have only minor neutralizing regions and, thus, can be very effective therapeutics for use in long-term treatment protocols. By employing the colony formation assays described above, the inventors have determined that VP2 capsids can inhibit growth of hematopoietic cells. (See FIG. 3). As above, human fetal liver cells were incubated in the presence of the VP2 capsids and the 11 day colony formation assay was performed. The positive control in this experiment was the native B19 VLP, that is, the B19 parvovirus capsids having 95% VP2 and 5% VP1 (VP1/2).

The results presented in FIG. 3 demonstrate that the VP2 capsids inhibit hematopoietic cell growth at concentrations as low as 3 μg/ml and significant inhibition occurs at 30 μg/ml. Embodiments suitable for long-term treatment can also comprise fragments of VP2 that are associated with the inhibition of cell growth (e.g., the P antigen binding site or regions of VP2 involved in fusion/internalization or both). As will be discussed in greater detail below, techniques in protein engineering, computer modeling, epitope mapping, and the "capsid agent characterization assays" described herein, can be employed to rapidly identify peptides of VP2 or VP1 or both that effectively inhibit cell growth without producing a potent immune response.

The term "capsid agent characterization assays" is intended to mean assays that analyze the ability of a "capsid agent" to inhibit the growth of a cell that has the P antigen. Examples of capsid agents include, but are not limited to, a B19 VLP or a VP1/2, or VP1 or VP2 capsid or modified or unmodified peptide fragments of VP1 or VP2 or both or synthetic molecules having sequences of VP1 or VP2 or both or peptidomimetics that resemble VP1 or VP2 or regions of either or both of these molecules. Examples of capsid agent characterization assays include, but are not limited to, colony formation assays, neutralization assays, protein binding or fusion assays, internalization assays, transcription or translation assays, and assays that evaluate the phosphorylation of proteins or calcium mobilization in a cell after contact with a capsid agent. (See also U.S. Pat. No. 5,508,186 to Young et al., herein expressly incorporated by reference, which describes several capsid agent characterization assays). In the next section, the inventors disclose the discovery that parvovirus B19 capsids can inhibit another type of cell that has the P antigen—the endothelial cell.

B19 Parvovirus Capsids Inhibit the Growth of Other Cells that Express the P Antigen Including, but not Limited to, Endothelial Cells The results from the first set of experiments provide evidence that parvovirus B19 capsids and VP2 capsids efficiently inhibit the growth of a number of different hematopoietic cells that have the P antigen (including hematopoietic cells from different species). In a second set of experiments, the inventors discovered that recombinant B19 parvovirus capsids inhibit the growth of another type of cell that has the P antigen. More specifically, the inventors found that parvovirus B19 capsids can inhibit the growth of endothelial cells, as evidenced by a reduction in endothelial cell proliferation and migration. A description of these experiments is provided below.

To determine whether B19 parvovirus capsids can inhibit endothelial cell proliferation, assays were performed in which primary human umbilical vein endothelial cells, plated at density of $1.5\times10^4$ cells per well in a 24 well plate, were incubated with B19 parvovirus capsids in the presence of 0.5% fetal calf serum +10.0 ng/ml basic fibroblast growth factor. The various B19 capsid preparations (i.e., VP1/2 or capsids made with only VP1 or VP2) were added to each well on the following day and the cells with capsids were incubated for additional 72 hours. Cell proliferation was then determined by using a crystal violet dye assay. Accordingly, capsid treated cells were washed in PBS, fixed in 3.7% formaldehyde, and incubated with crystal violet. The dye was then removed by extensive washes with distilled water. The cell-associated crystal violet was solubilized with 10% acetic acid and quantified at absorbance 540 nm in an ELISA plate reader.

In FIGS. 4–7 are shown the results of the endothelial cell proliferation assays. The "x axis" of these figures has an increasing concentration of control antigen KYVTGIN (SEQ. ID. NO. 1) (FIG. 4), B19 parvovirus capsid (VP1 alone) (FIG. 5), B19 parvovirus capsid (VP1/2) FIG. 6), and B19 parvovirus capsid (VP2 alone) (FIG. 7). Thus, from left to right, the bars represent the absorbance at 540 nm with 0 µg/ml, 0.01 µg/ml, 0.1 µg/ml, 1.0 µg/ml, and 10.0 µg/ml. The "y axis" shows a standard of absorbance values at 540 nm. The standard deviation was with in 10%. As shown in FIG. 7, the VP2 capsids efficiently inhibited endothelial cell proliferation at concentrations as low as 1.0 µg/ml and significant inhibition was observed at 10.0 µg/ml.

Figure 8:
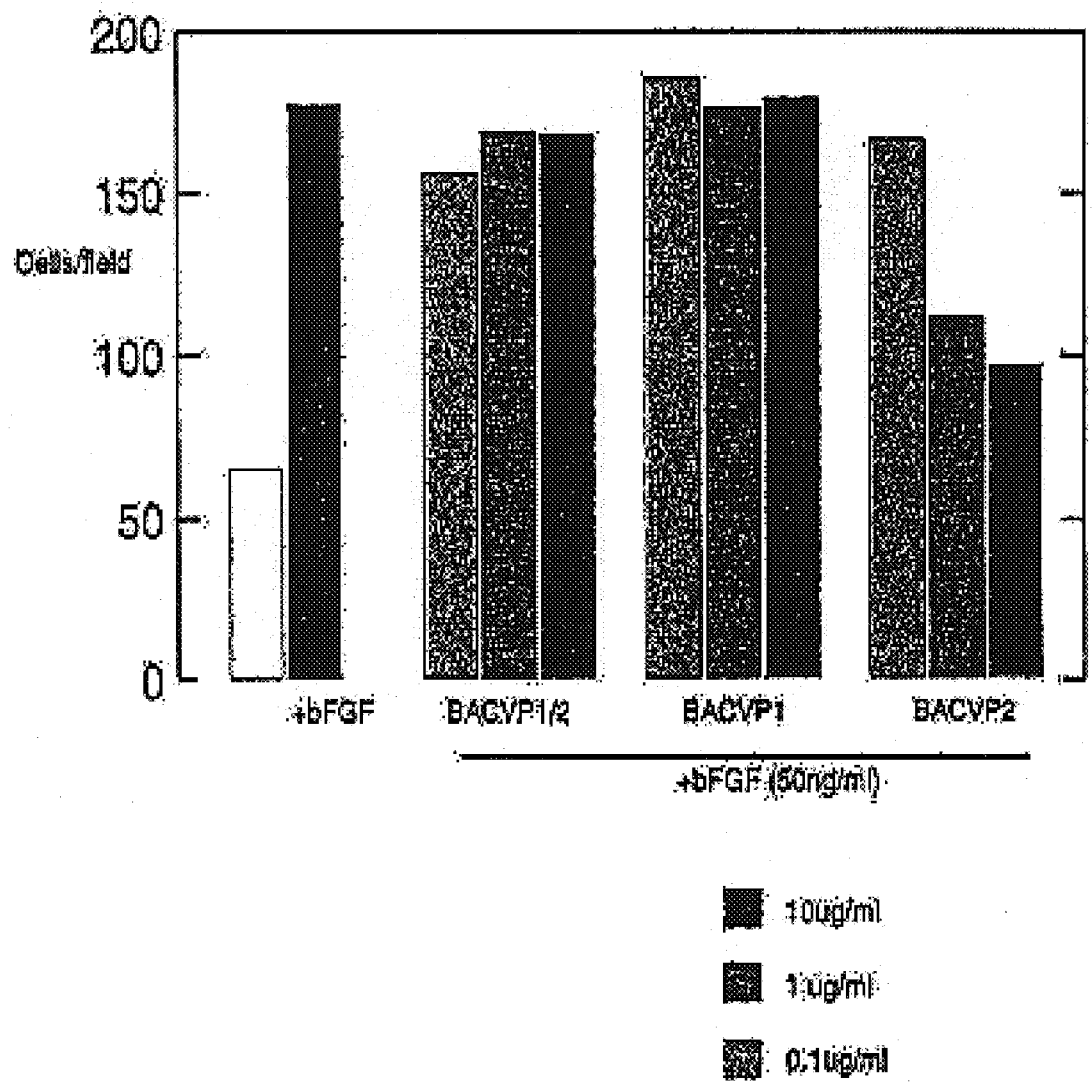
FIG. 8 This figure shows a bar graph that represents the results of cell migration assays performed on human umbilical vein endothelial cells (HUVEC) that were contacted with varying concentrations of B19 parvovirus capsids (VP1/2), B19 parvovirus capsids having only VP1 (VP1 only), B19 parvovirus capsids having only VP2 (VP2 only), or a control antigen (control antigen).

The effect of B19 parvovirus capsid preparations on cell migration was also determined. The migration assays were performed using a modified Boyden chamber assay (Neuroprobe, Inc.). Basic fibroblast growth factor (40ng/ml) was added to stimulate migration of the HUVEC cells through a collagen 1 coated 8 µm pore size millipore filter. Cells were incubated for 60 min with the various B19 capsid preparations (i.e., VP1/2 or capsids made with only VP1 or VP2) prior to conducting the migration assay. To perform the migration assay, the Boyden chamber was incubated for 4.5 h at 37° C. in a 10% $CO_2$ atmosphere. The filters were subsequently removed and were fixed in 3.7% formaldehyde. Cell migration was visualized by staining the filters overnight in Gill's Hematoxylin. The number of migrating cells were scored by counting stained cells on the migrating side of the filter per high power magnification field. (See FIG. 8). As shown in FIG. 8, VP2 capsids at concentrations as low as 1 µg/ml effectively inhibited endothelial cell migration. Further, the VP2 capsid-mediated inhibition of endothelial cell migration was significantly more potent than that observed with either native capsids (VP1/2) or capsids having only VP1.

The results from the experiments described above provide evidence that parvovirus B19 capsids, modified parvovirus B19 capsids, and VP2 capsids can be manufactured and used to efficiently inhibit the growth and/or migration of cells that have the P antigen, such as cells of hematopoietic origin and endothelial cells. The experiments above also reveal that B19 capsid protein sequences that bind the P antigen and/or are involved in fusion or internalization of the particle can be involved in inhibiting cell growth or cell migration. While these embodiments are suitable for many of the therapeutic applications of the invention, pharmaceuticals comprising fragments of VP1 or VP2 or both or synthetic molecules can be constructed to more efficiently bind, fuse, and internalize with cells that have the P antigen. In the section below, the inventors teach the manufacture and characterization of more capsid agents that inhibit cell growth and cell migration.

B19 Capsid Agents that Inhibit Growth and Migration of Cells that Have the P Antigen In this section, the inventors describe several techniques that can be used to manufacture, design, and characterize capsid agents, including but not limited to, parvovirus B19 capsids, modified parvovirus B19 capsids, VP2 capsids, and peptides or peptidomimetics that have sequences that correspond to regions of either VP1, VP2, or both. The VP1 and VP2 structural gene has been sequenced in its entirety and this sequence can be obtained from the NCBI database source accession number U38506.1, or accession number AAB47788, or medline number 97081188, or as published by Erdman et al., *J Gen. Virol.*, 77: 2767 (1996), all references and sequences therein are hereby expressly incorporated by reference. The VP1 or VP2 or fragments of either or both used with embodiments of the invention correspond to sequences involved in the inhibition of cell growth and cell migration. Desirable peptides of the invention can comprise between three amino acids and 780 amino acids of the VP1 and VP2 structural protein but have at least some portion of the molecule that is involved in the inhibition of growth and/or migration of cells that have the P antigen. In other words, preferable embodiments of the invention can include at least three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety or one-hundred amino acids of the VP1 and VP2 structural gene. Desirable embodiments can include at least 110, 120, 130, 140, 150, 160, 170, 180, 190, 200, 210, 220, 230, 240, 250, 260, 270, 280, 290, 300, 310, 320, 330, 340, 350, 360, 370, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, or 780 amino acids of the VP1 and VP2 structural protein.

The peptides and fragments or derivatives thereof that are involved in the inhibition of growth and migration of cells that have the P antigen, include but are not limited to, those regions of the VP1 and VP2 structural gene that is found in nature. Additionally, altered sequences in which functionally equivalent amino acid residues are substituted for residues within the sequence resulting in a silent change can also be present in these capsid agents. Accordingly, one or more amino acid residues within the sequence of the VP1 and VP2 structural gene can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic aminoacids include phenylalanine, tryptophan, and tyrosine. The peptides described above are preferably analyzed in assays to determine whether the fragment has retained the ability to inhibit the growth and/or migration of cells that have the P antigen.

Peptides for use in aspects of the invention can also be modified, e.g., the peptides can have substituents not normally found on a peptide or the peptides can have substituents that are normally found on the peptide but are incorporated at regions of the peptide that are not normal. These peptides can be acetylated, acylated, or aminated, for example. Substituents that can be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. Additionally, VP1 or VP2 or fragments of either or both can be derivatized in that the derivative polypeptide can be manipulated to include aminoacid sequences that effect the function and stability of the molecule. For example, peptides that are involved in the inhibition of growth and migration of cells that have the P antigen can be engineered to have one or more cysteine residues so as to promote the formation of a more stable derivative through disulfide bond formation. (See e.g., U.S. Pat. No. 4,908,773). Computer graphics programs and the assays described herein can be employed to identify cystine linkage sites that provide greater stability but do not perturb the ability to inhibit growth or migration of cells that have the P antigen. (See e.g., Perry, L. J., & Wetzel, R., *Science*, 226:555–557 (1984); Pabo, C. O., et al., *Biochemistry*, 25:5987–5991 (1986); Bott, R., et al., European Patent Application Ser. No. 130,756; Perry, L. J., & Wetzel, R., *Biochemistry*, 25:733–739 (1986); Wetzel, R. B., European Patent Application Ser. No. 155,832).

Additional derivatives that are embodiments of the invention include peptidomimetics that resemble regions of VP1, VP2, or both. Synthetic peptides can be prepared that correspond to these molecules by employing conventional synthetic methods, utilizing L-amino acids, D-amino acids, or various combinations of amino acids of the two different configurations. Synthetic compounds that mimic the conformation and desirable features of a particular peptide but avoid the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2 S$] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2NH$] and hydroxyethylene [$CHOHCH_2$] bioisosteres at the Leu-Val amide bond in the 6–13 octapeptide derived from angiotensinogen). Numerous methods and techniques are known in the art for designing and manufacturing peptidomimetcs, any of which could be used. (See, e.g., Farmer, P. S., Drug Design, (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396; Kaltenbronn et al., in J. Med. Chem. 33: 838–845 (1990); and Spatola, A. F., in Chemistry and Biochemistry of Amino Acids. Peptides, and Proteins, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of beta.-sheets and alpha.-helices in Peptides," Tibech, Vol. 8, pp. 249–255 (1990). Additional teachings can be found in U.S. Pat. Nos. 5,288,707; 5,552,534; 5,811,515; 5,817,626; 5,817,879; 5,821,231; and 5,874,529, herein incorporated by reference. Accordingly, peptidomimetics of the invention can have structures that resemble at least three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety, one-hundred, 110, 120, 130, 140, 150, 160, 170, 180, 190, 200, 210, 220, 230, 240, 250, 260, 270, 280, 290, 300, 310, 320, 330, 340, 350, 360, 370, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, or 780 amino acids of the VP1 and VP2 structural protein so long as some region of the molecule inhibits the growth or migration of a cell that has the P antigen.

Conventional techniques in molecular biology, such as those described in U.S. Pat. No. 5,508,186, herein expressly incorporated by reference in its entirety, can be used to prepare numerous types of capsid agents. The term "capsid agents" can refer to capsids comprising VP1, VP2, VP1/2 in varying proportions, fragments of VP1 or VP2 or either or both, fusion proteins having sequences that correspond to VP1 or VP2 or both, and modified or unmodified proteins or peptides or peptidomimetics that correspond to sequences of the VP1 and VP2 structural gene that are involved in the inhibition of growth and/or migration of cells that have the P antigen.

By the approach described in U.S. Pat. No. 5,508,186 a capsid agent can be manufactured as follows. Plasmids can be constructed to contain either full length VP1 or VP2 or both. To construct plasmid pVP1/941, a cDNA encoding the VP1 gene can be excised from pYT103c, a nearly full length molecular clone of B19 parvovirus (Cotmore et al. Science 226:1161 (1984); Ozawa et al. J. Virol. 62:2884)1988)), by digestion with the restriction enzymes Hind III (which cuts at map unit 45) and EcoRI (which cuts at map unit 95) followed by treatment with mung bean nuclease to complement single stranded ends. The resultant DNA fragment is then inserted into the BamHI site (made blunt ended with the Klenow fragment of DNA polymerase) of the baculovirus transfer vector pVL941, a vector derived by deletion of the polyhedrin gene of AcMNPV (Autographa california nuclear polyhedrosis virus) followed by cloning into the pUC8 plasmid (Summers et al. Tex. Agric. Exp. Stn. 1555 (1987)). Construction of pVP2/941 is performed by the insertion of a PstI-EcoRI digestion fragment of pYT103c (map units 58–95; the EcoRI site was blunt-ended) and a synthetic DNA fragment of 20 nucleotides corresponding to the SstI-PstI region (again with the SstI site blunt-ended) into the BamHII site of pVL941. Additionally, the Polymerase Chain Reaction (PCR) can be used to clone the VP1 or VP2 gene or portions thereof from full-length clones as described by Erdman et al., *J Gen Virol.* 77:2767 (1996), herein incorporated by reference in its entirety. To facilitate cloning, the primers can be designed to generate convenient sites for restriction digestion, as is known in the art.

Recombinant plasmids encoding VP1, VP2, VP1/2, or fragments thereof are then transfected into insect cells to generate recombinant baculoviruses. Accordingly, 8 $\mu$g of the recombinant plasmid is cotransfected into Sf9 cells with 2 $\mu$g of wild type AcMNPV, using calcium phosphate-mediated precipitation. The Sf9 cell line (American Type Culture Collection, Rockville Md.), which is derived from Spodoptera frugiperda (fall army worm) ovary, is maintained in Grace's insect tissue culture medium containing 10% heat inactivated fetal bovine serum, 2.5 $\mu$g/ml fungizone, 50 $\mu$/ml gentamicin, 3.33 mg/ml lactalbumin hydrolysate, and 3.33 mg/ml yeastolate (provided complete by Gibco BRL Life Technologies, Gaithersburg Md.) at 100% room air, 95% humidity, at 27° C. Six days after transfection, progeny virus is harvested and replaqued onto fresh Sf9 cells. Recombinant viruses are recognized visually by the absence of occlusion bodies in the nucleus of cells (the occlusion-positive phenotype is the result of synthesis of large quantities of the polyhedrin protein). Recombinant viruses can be subjected to three cycles of plaque purification before large scale VLP stocks are prepared and isolated or purified. Purified compositions containing 0.1%, 0.5%, 1%, 2%, 5%, 10%, 25%, or more (weight/weight) of the active ingredient are specifically contemplated.

The term "isolated" requires that the material be removed from its original environment (e.g., the natural environment if it is naturally occurring). For example, a naturally occurring protein present in a living cell is not isolated, but the same protein, separated from some or all of the coexisting materials in the natural system, is isolated. The term "purified" does not require absolute purity; rather it is intended as a relative definition. For example, proteins are routinely purified to electrophoretic homogeneity, as detected by Coomassie staining, and are suitable in several assays despite having the presence of contaminants. Preferably, capsid agent characterization assays are performed on the isolated or purified capsid agents including, but not limited to, the assays described in U.S. Pat. No. 5,508,186 (e.g., DNA, RNA, and proten analysis, immunoblots, immunofluorescence, sedimentation analysis, electron microscopy, immune electron microscopy, and the capsid agent characterization assays described previously.

In some embodiments, particularly for applications that involve the long-term administration of capsid agents, it is desirable to manufacture a pharmaceutical that does not elicit a significant immune response in a subject. A general scheme for the manufacture of capsid agents that do not induce an immune response involves design of the agent, construction of the agent, analysis of the agent's ability to inhibit cell growth and/or cell migration and an analysis of the immune response generated to the agent. Many of the immunogenic regions of the parvovirus B19 capsid are known and, through conventional techniques in molecular biology, these immunogenic regions can be deleted, mutagenized, or modified and the newly designed synthetic capsid proteins can be analyzed in one or more capsid agent characterization assays (e.g., a colony formation assay and a neutralization assay using sera generated from asymptomatic individuals). Many methods can be employed to identify the immunogenic regions of the B19 parvovirus capsid and manufacture non-immunogenic VLPs that inhibit cell growth and/or migration and the example below is provided as one possible approach.

Test expression constructs can be designed, manufactured, and analyzed as follows. This process can be iterative so as to generate several classes of VLPs and pharmaceuticals having these capsid agents, which differ according to their ability to inhibit cell growth, cell migration, and induce an immune response in a subject. Accordingly, by one approach, the VP2 structural gene can be cloned from clinical isolates using PCR with primers designed from the published VP2 sequence. The VP2 gene is subsequently subcloned both into BlueScript (Pharmacia) for mutagenesis, and pVL1393 (Stratagene) for expression in Sf9 cells. Mutations that correspond to immunogenic regions of VP2 (e.g., amino acids 253–272, 309–330, 328–344, 359–382, 449–468, and 491–515) are introduced into the VP2 gene using Amersham Sculptor in vitro mutagenesis kit. One of skill in the art will appreciate that carboxy truncations, amino truncations, internal truncations, and site-directed mutagenesis of the VP1 and VP2 structural protein can be accomplished by several approaches. Preferably, several different clones having one or more of the deletions described above are generated. The appearance of a desired mutation is confirmed by sequencing and the mutated gene is then subcloned into pVL1393 for expression in Sf9 cells. The SF9 cells are then transfected using BaculoGold Transfection kit (Pharmingen). Transfections can be performed according to the manufacturer's instructions with the following modifications. Approximately, $8 \times 10^8$ Sf9 cells are transfected in a 100 mM dish, with 4 µg of BaculoGold DNA and 6 µg of test DNA. Cells are harvested after 6 days and assayed for VLP production.

Next, cells are harvested by scraping followed by low speed centrifugation. Cells are then resuspended in 300 ml of breaking buffer (1 M NaCl, 0.2 M Tris pH 7.6) and homogenized for 30" on ice using a Polytron PT 1200 B with a PT-DA 1205/2-A probe (Brinkman) in a Falcon 1259 tube. Samples are spun at 2500 rpm for 3 minutes to pellet debris and the tubes are washed with an additional 150 ml of breaking buffer. The supernatants are collected in a 1.5 ml microfuge tubes and are re-spun for 5 minutes in an Eppendorf microfuge (Brinkman). The collected supernatants can be stored at 4° C.

ELISA assays can then be performed on the isolated VLPs as follows. Approximately, 5 ml of extract is diluted into 50 ml of 1% BSA in PBS (phosphate buffered saline; 20 mM $NaPO_4$, pH 7.0, 150 mM NaCl) and is plated onto a polystyrene plate. The plate is incubated overnight at 4° C. Extracts are removed and the plate is blocked with 5% powdered milk in PBS. All subsequent wash steps are performed with 1% BSA in PBS. The plate is incubated at room temperature with primary antibody for 1 hour (e.g., sera generated from asymptomatic individuals). After washing to remove unbound antibody, plates are incubated for 1 hour with secondary antibody. The secondary antibody, peroxidase labeled Goat anti-Mouse IgG (g), can be purchased from Kirkegaard & Perry Laboratories, Inc. and can be used at $10^3$ dilution in 1% BSA in PBS. After a final washing, an alkaline phosphatase assay is performed and absorbance is read at 405 nm. The most'successful capsid agents by this assay will be ones that evade detection. That is, desired mutant VP2 capsids are ones that have lost epitopes recognized by antibodies present in the sera and, thus, are not detected by the ELISA. By performing these experiments with several lots of sera obtained from different individuals and the monoclonal antibodies that neutralize the inhibition of colony formation or cell migration, one of skill can rapidly identify the regions of VP2 that are immunogenic and mutant VP2 capsids that best evade an immune response.

Next, the mutant VP2 capsids that successfully evade detection by the ELISA method described above are analyzed for their ability to inhibit cell growth and cell migration by using a capsid agent characterization assays. By assessing each mutant VP2 capsid's ability to inhibit cell growth and cell migration and coordinating this information with the immunogenicity results from the ELISA analysis, "a capsid agent profile" can be generated. A "capsid agent profile" can include a symbol or icon that represents a mutant capsid protein or mutant VLP, sequence information (e.g., the location of mutations or modifications), a capsid agent class designation (e.g., information regarding relationships to other capsid agents), application information (e.g., disease indications or treatment information, or clinical or biotechnological uses), and performance information from capsid agent characterization assays (e.g., values obtained from the colony formation assays, neutralization assays, fusion/internalization assays, binding assays, phosphorylation assays, cell migration assays, proliferation assays, and results obtained from immunogenicity analysis including the ELISA assays).

Capsid agent profiles can be recorded on a computer readable media, stored in a database, on hardware, software, or memory, accessed with a search engine and can be compared with one another or associated with a disease state or "disease state profile", which is information relating to a disease, condition or indicated treatment. These capsid agent profiles and disease state profiles can be used by investigators for rational drug design or biochemical analysis or by physicians or clinicians who wish to choose an appropriate pharmaceutical composition that balances the optimal level of cell growth and cell migration inhibition with immune response of the subject in light of the desired duration of treatment.

In several embodiments, the capsid agents are disposed on a support so as to create a multimeric capsid agent. While a monomeric agent (that is, an agent that presents a discrete molecule, thus, carrying only one binding domain) can be sufficient to achieve a desired response, a multimeric agent (that is, an agent that presents multiple molecules, thus, having several domains) often times can elicit a greater response. It should be noted that the term "multimeric" refers to the presence of more than one molecule on an support, for example, several individual molecules of VP2 joined to a support, as distinguished from the term "multimerized" that refers to an agent that has more than one molecule joined as a single discrete compound molecule on a support, for example several molecules of VP2 joined to form a single compound molecule that is joined to a support. A multimeric form of the capsid agents described herein can be advantageous for many biotechnological or clinical applications because of the ability to obtain an agent with higher affinity for a cell having the P antigen.

A multimeric capsid agent can be obtained by coupling the protein, for example, VP2 or a fragment thereof to a macromolecular support. A "support" may also be termed a carrier, a resin or any macromolecular structure used to attach or immobilize a protein. The macromolecular support can have a hydrophobic surface that interacts with regions of the capsid agent by hydrophobic non-covalent interactions. The hydrophobic surface of the support can be, for example, a polymer such as plastic or any other polymer in which hydrophobic groups have been linked such as polystyrene, polyethylene, PTFE, or polyvinyl. Alternatively, capsid agents can be covalently bound to carriers including proteins and oligo/polysaccarides (e.g. cellulose, starch, glycogen, chitosane or aminated scpharose). In these later embodiments, a reactive group on capsid agent, such as a hydroxy or the amino present in the peptide, can be used to join to a reactive group on the carrier so as to create the covalent bond. Embodiments also can comprise a support with a charged surface that interacts with the capsid agent. Additional embodiments concern a support that has other reactive groups that are chemically activated so as to attach a capsid agent. For example, cyanogen bromide activated matrices, epoxy activated matrices, thio and thiopropyl gels, nitrophenyl chloroformate and N-hydroxy succinimide chlorformate linkages, or oxirane acrylic supports can be used. (SIGMA).

Further, the support can comprise inorganic carriers such as silicon oxide material (e.g. silica gel, zeolite, diatomaceous earth or aminated glass) to which the capsid agent is covalently linked through a hydroxy, carboxy or amino group of the peptide and a reactive group on the carrier. Thus, in appropriate contexts, a "support" can refer to the walls or wells of a reaction tray, test tubes, catheters, stents, balloons, prosthetics, medical devices, polystyrene beads, magnetic beads, nitrocellulose strips, membranes, microparticles such as latex particles, sheep (or other animal) red blood cells, Duracyte® artificial cells, and others. Inorganic carriers, such as silicon oxide material (e.g. silica gel, zeolite, diatomaceous earth or aminated glass) to which the capsid agents are covalently linked through a hydroxy, carboxy or amino group and a reactive group on the carrier are also embodiments. Carriers for use in the body, (e.g., for prophylactic or therapeutic applications) are preferably physiological, non-toxic and non-immunoresponsive. Such carriers include, but are not limited to, poly-L-lysine, poly-D, L-alanine and Chromosorb® (Johns-Manville Products, Denver Co.).

In other embodiments, linkers, such as A linkers or biotin-avidin (or streptavidin), of an appropriate length are inserted between the capsid agent and the support so as to encourage greater flexibility and thereby overcome any steric hindrance that is presented by the support. The determination of an appropriate length of linker that allows for optimal interaction is made by screening the capsid agents having varying length linkers in the capsid agent characterization assays described herein.

In other embodiments, the multimeric supports discussed above have attached multimerized capsid agents so as to create a "multimerized-multimeric support". An embodiment of a multimerized capsid agent is obtained by creating an expression construct having two or more nucleotide sequences encoding VP2 or a fragment thereof, for example, joined together. The expressed fusion protein is one embodiment of a multimerized capsid agent and is then joined to a support. A support having many such multimerized agents is termed a multimerized-multimeric support. Linkers or spacers between the domains that make-up the multimerized agent and the support can be incorporated for some embodiments and optimally spaced linkers can be determined using the capsid agent characterization assays.

In some embodiments, capsid agents are disposed on prosthetic devices that are implanted into a subject. With many types of prosthetics, for example, stents and valves, a limited amount of tissue ingrowth is desired so as to stabilize the implant. During implantation, however, the injury to surrounding tissue results in a considerable increase in cellular proliferation, which can cause fibrotic build up or restenosis and, over time, constriction of a stent or repositioning of a valve. Prior art devices have sought to overcome this problem through the use of radioactivity, however, the treatment success and potential for systemic exposure to the radioactive substances that are released from the device makes such approaches less than desirable. Similarly, oftentimes techniques such as balloon angioplasty result in restenosis caused by the infiltration of endothelial cells.

By attaching capsid agents to medical prosthetics, such as stents or valves, or delivering capsid agents through porous catheters (e.g., balloon cathers as used in angioplasty) endothelial cell migration, proliferation, fibrotic build up, tissue ingrowth, and restenosis can be efficiently inhibited. Further, a delayed tissue ingrowth can be obtained by using capsid agents that are cleared by the immune system at a time after the inflammation associated with the medical procedure has quelled. By using the approaches described above, capsid agents can be attached to many different types of prosthetics, e.g., stents or valves, through hydrophobic interactions or covalent linkages. Further, cathers in the prior art can be adapted for the delivery of capsid agents to the site of angioplasty. By analyzing the capsid agent profiles, a physician can select the appropriate capsid agent-coated prosthetic for implantation or the appropriate capsid agent for delivery depending on the desired time of cell inhibition or delay in tissue ingrowth. Localized delivery of capsid agents in other manners is also contemplated. Thus, for example, growth of vascular endothelial cells can be inhibited by implanting a controlled release composition in the vicinity of a stent, graft, valve, or other prosthetic, or by delivering the drug to the site via infusion pump or other suitable device. In addition to coatings for medical devices and formulations for catheter delivery, the capsid agents described herein can be formulated in pharmaceuticals and used to treat or prevent human diseases or conditions associated with proliferation or migration of cells that have the P antigen. The section below discusses the many ways to formulate capsid agents into pharmaceuticals and determine an appropriate dose.

The Manufacture and Dose of Therapeutic and Prophylactic Agents

The capsid agents of the invention (e.g., VP1, VP1/2, VP2 or fragments thereof) are suitable for treatment of subjects either as a preventive measure to avoid a disease or condition, or as a therapeutic to treat subjects already afflicted with a disease. These pharmacologically active compounds can be processed in accordance with conventional methods of galenic pharmacy to produce medicinal agents for administration to subjects, e.g., mammals including humans. The active ingredients can be incorporated into a pharmaceutical product with and without modification. Further, the manufacture of pharmaceuticals or therapeutic agents that deliver the pharmacologically active compounds of this invention by several routes are aspects of the invention. For example, and not by way of limitation, DNA, RNA, and viral vectors having sequence encoding the capsid agents are used with embodiments. Nucleic acids encoding capsid agents can be administered alone or in combination with other active ingredients. The compounds of this invention can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's Pharmaceutical Sciences,* 15th Edition, Easton:Mack Publishing Company, pages 1405–1412 and 1461–1487(1975) and *The National Formulary* XIV, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation can vary based on the individual patient and the type and stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population). The Macaque or Babboon are appropriate experimental models, as described earlier. The data obtained from cell culture assays and animal studies is used in formulating a range of dosage for human use. The dosage of such compounds lies preferably within a range of circulating concentrations that include the ED50 with no toxicity. The dosage varies within this range depending upon type of capsid agent, the dosage form employed, sensitivity of the patient, and the route of administration.

Normal dosage amounts may vary from approximately 1 to 100,000 micrograms, up to a total dose of about 10 grams, depending upon the route of administration. Desirable dosages include 250 μg, 500 μg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the concentrations of the capsid agents can be quite high in embodiments that administer the agents in a topical form. Molar concentrations of capsid agents can be used with some embodiments. Desirable concentrations for topical administration and/or for coating medical equipment range from 100 μM to 800 mM. Preferable concentrations for these embodiments range from 500 μM to 500 mM. For example, preferred concentrations for use in topical applications and/or for coating medical equipment include 500 μM, 550 μM, 600 μM, 650 μM, 700 μM, 750 μM, 800 μM, 850 μM, 900 μM, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM.

In some embodiments, the dose of capsid agent preferably produces a tissue or blood concentration or both from approximately 0.1 μM to 500 mM. Desirable doses produce a tissue or blood concentration or both of about 1 to 800 μM. Preferable doses produce a tissue or blood concentration of greater than about 10 μM to about 500 μM. Preferable doses are, for example, the amount of capsid agent required to achieve a tissue or blood concentration or both of 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 145 μM, 150 μM, 160 μM, 170 μM, 180 μM, 190 μM, 200 μM, 220 μM, 240 μM, 250 μM, 260 μM, 280 μM, 300 μM, 320 μM, 340 μM, 360 μM, 380 μM, 400 μM, 420 μM, 440 μM, 460 μM, 480 μM, and 500 μM. Although doses that produce a tissue concentration of greater than 800 μM are not preferred, they can be used with some embodiments of the invention. A constant infusion of the capsid agent can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease state of the patient, age, and weight of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the pharmaceuticals of the invention include, but are not limited to, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically active compounds of this invention that are suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having the pharmacologically active compounds of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the pharmacologically active compounds of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Compositions having the pharmacologically active compounds of this invention that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the capsid agent has been obtained, it can be administered to a subject in need to treat or prevent diseases or conditions associated with proliferation or migration of a cell that has the P antigen.

Aspects of the invention also include a coating for medical equipment such as prosthetics, implants, and instruments. Coatings suitable for use in medical devices can be provided by a gel or powder containing the capsid agents or by polymeric coating into which the capsid agents are suspended. Suitable polymeric materials for coatings or devices are those that are physiologically acceptable and through which a therapeutically effective amount of the capsid agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. that is incorporated herein by reference in its entirety. In the section below, the inventors disclose several methods to treat diseases or conditions associated with proliferation or migration of a cell that has the P antigen, which involve providing a pharmaceutical having a capsid agent.

Therapeutic and Prophylactic Approaches

In several aspects of the invention, capsid agents, in particular pharmaceuticals having capsid agents, are provided to a subject in need to treat or prevent a disease or condition associated with abnormal cell proliferation and/or cell migration. Methods to formulate pharmaceuticals for the inhibition of growth or migration of cells that have the P antigen, including, but not limited to, hematopoietic cells and endothelial cells, are embodiments of the invention. That is, embodiments of the invention include the use of medicaments comprising a capsid agent for the inhibition of growth and/or migration of cells that have the P antigen, such as hematopoeitic cells and endothelial cells.

In one embodiment, capsid agents can be used to inhibit hematopoesis in recipient subjects prior to in utero stem cell transplantation. In a previous study on tissue distribution of stem cells in the human fetus, it was estimated that a fetal transplantation with $5\times10^7$ cells in the second trimester would produce a donor-to-recipient ratio of approximately 1:1000–1:10000. Such a low ratio fails to provide transplanted cells with a competitive edge over the native stem cells. (Westgren et al., *Am J Obstet Gynecol,* 176:49 (1996)). To improve this ratio and the success of stem cell transplantation, capsid agents can be administered prior to transplantation so as to suppress the native stem cell population and thereby improve the transplantation. Furthermore, treatment of donor stem cells with anti-P monoclonal antibodies prior to transplantation can protect them from suppression by the capsid agents, and thereby provide an even more favorable status. Thus, one embodiment includes a medicament comprising a capsid agent for treatment of a patient prior to stem cell transplantation. This method of treatment can be performed by identifying a subject in need of an in utero stem cell transplantation and providing to said subject a therapeutically beneficial amount of a capsid agent that inhibits hematopoietic cell growth.

In a similar aspect of the invention, a method non-myeloablative conditioning prior to postnatal stem cell transplantation is embodied. Recently, methods of nonmyeloblative conditioning have received considerable attention because such protocols are less toxic to the patients than the standard approach, which involves high-dose chemoradiotherapy. (Giralt et al., *Blood,* 89:4531 (1997); Slavin et al., *Blood,* 91:756 (1998)). However, complete donor hematopoietic chimerism using existing techniques in non-myeloablative therapy has not been very successful. By providing capsid agents prior to postnatal stem cell transplantation, the ratio of donor cells to recipient cells can be favorably skewed and donor hematopoietic chimerism can be achieved with out radiation. Accordingly, a method of non-myeloablative conditioning can be performed by identifying a subject in need of non-myeloablative conditioning prior to postnatal stem cell transplantation and administering to said subject a therapeutically beneficial amount of a capsid agent.

Still another aspect of the invention is directed to a method of treating a subject suffering from an hematological proliferative disorders, e.g., polycytemia vera. Polycythemia Vera (PCV) is a haematological disease caused by an uncontrolled proliferation of red blood cells in the bone marrow. Cells of other lineage (leukocytes and thrombocytes) are involved but do not give rise to complications of similar severity. The disease is seen in middle-aged and aged individuals (median age at diagnosis is 60 years) and the incidence in Sweden is 1.5 cases per 100.000 inhabitants. To date, there is no specific pharmacological treatment and current approaches to the problem seek to ease the symptoms of the slowly progressing disease. Median survival time without treatment is short. In younger individuals, with optimal treatment, one can obtain a reasonable quality of life for periods up to 20 years.

By administering capsid agents to subjects suffering from PCV, the proliferation of hematopoietic cells can be inhibited and an effective treatment for this deadly disease can be provided. Accordingly, a method of PCV can be performed by identifying a subject in need of treatment for PCV and administering to said subject a therapeutically beneficial amount of a capsid agent. Because a long-term treatment protocol is envisioned, preferably, the capsid agents used are ones that elicit a minimal immune response.

Yet another aspect of the invention is directed to a method of treating a patient for inhibition of endothelial cell growth. As described above, undesired endothelial cell growth can occur after surgical trauma, e.g., after the implantation of a valve, stent or other prosthetic or angioplasty, in said patient. Additionally, tumor development and metastasis requires endothelial cell growth and cell migration. Thus, embodiments of the invention concern medicaments that inhibit cancer, more specifically, angiogenesis and the cell migration events associated with metastasis.

Angiogenesis concerns the formation of new capillary blood vessels by a process of sprouting from pre-existing vessels. Angiogenesis occurs during development, as well as in a number of physiological and pathological settings, and is necessary for tissue growth, wound healing, female reproductive function, and is a component of pathological processes such as hemangioma formation and ocular neovascularization. However, much of the longstanding interest in angiogenesis comes from the discovery that solid tumors must undergo angiogenesis inorder to grow beyond a critical size. That is, tumors must recruit endothelial cells from the surrounding stroma to form their own endogenous microcirculation.

By administering capsid agents to subjects suffering from cancer, the proliferation and migration of endothelial cells can be inhibited and, thus, tumorigenesis and metastasis can be prevented. Accordingly, a method of inhibiting angiogenesis, tumorigenesis, or cancer can be performed by identifying a subject in need of an inhibition in angiogenesis, tumorigenesis, or cancer and administering to said subject a therapeutically beneficial amount of a capsid agent. Because a long-term treatment protocol is envisioned, preferably, the capsid agents used are ones that elicit a minimal immune response.

Additional embodiments of the invention include kits containing capsid agents, and written instructions for dosage and administration to a patient for hematopoietic progenitor cell growth inhibition, instructions for dosage and administration for hematopoietic progenitor cell growth inhibition in a patent prior to stem cell transplantation to said patient, such as a fetus, instructions for dosage and administration to a patient for endothelial cell growth inhibition and/or instructions for dosage and administration to a patient suffering from hematological proliferative disorders of P antigen positive cells, e.g., polycytemia vera.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of inhibiting hematopoiesis of a hematopoietic cell comprising:

identifying a hematopoietic cell in need of an inhibition of hematopoiesis; and contacting said hematopoietic cell with an amount of a capsid agent comprising parvovirus B19 major capsid protein (VP2) sufficient to inhibit hematopoiesis, whereby said contact inhibits hematopoiesis of said hematopoietic cell.

2. The method of claim 1, wherein said capsid agent comprises parvovirus B19 minor capsid protein (VP1) and parvovirus B19 major capsid protein (VP2).

3. The method of claim 1, further comprising the step of measuring the inhibition of hematopoiesis.

4. A method of inhibiting hematopoeisis in a subject in need thereof comprising:

identifying a subject in need of an inhibition of hematopoiesis; and providing to said subject an amount of capsid agent comprising parvovirus B19 major capsid protein (VP2) sufficient to inhibit hematopoiesis, whereby hematopoiesis in said subject is inhibited.

5. The method of claim 4, wherein said capsid agent comprises parvovirus B19 minor capsid protein (VP1) and parvovirus B19 major capsid protein (VP2).

6. The method of claim 4, wherein said subject in need is identified as having a hematological proliferative disorder.

7. The method of claim 6, wherein said hematological proliferative disorder is polycythemia vera.

8. The method of claim 4, further comprising the step of measuring the inhibition of hematopoiesis.

* * * * *

```
                        SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Artificial Control Peptide

<400> SEQUENCE: 1

Lys Tyr Val Thr Gly Ile Asn
  1               5
```